(12) United States Patent
Hwang et al.

(10) Patent No.: US 7,107,087 B2
(45) Date of Patent: Sep. 12, 2006

(54) METHOD AND APPARATUS FOR MEASURING A CONCENTRATION OF A COMPONENT IN A SUBJECT

(75) Inventors: In-duk Hwang, Suwon-si (KR); Gil-won Yoon, Seoul (KR); Sang-joon Han, Seoul (KR); Kye-jin Jeon, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 236 days.

(21) Appl. No.: 10/801,612

(22) Filed: Mar. 17, 2004

(65) Prior Publication Data

US 2004/0186361 A1  Sep. 23, 2004

(30) Foreign Application Priority Data

Mar. 17, 2003  (KR) ............. 10-2003-0016406

(51) Int. Cl.
*A61B 5/00* (2006.01)
*G01J 3/42* (2006.01)

(52) U.S. Cl. ............. 600/310; 356/327; 250/338.1; 250/341.3

(58) Field of Classification Search .......... 600/309, 600/310, 322; 250/339, 338.1, 341; 356/346, 356/327
See application file for complete search history.

(56) References Cited

U.S. PATENT DOCUMENTS

| | | | |
|---|---|---|---|
| 4,771,629 A | 9/1988 | Carlson et al. | |
| 5,039,855 A | 8/1991 | Kemeny et al. | |
| 5,086,229 A | 2/1992 | Rosenthal et al. | |
| 5,222,495 A | 6/1993 | Clarke et al. | |
| 5,372,135 A | 12/1994 | Mendelson et al. | |
| 5,477,321 A * | 12/1995 | Johnson ..................... | 356/327 |
| 5,655,530 A * | 8/1997 | Messerschmidt ........... | 600/366 |
| 6,152,876 A | 11/2000 | Robinson et al. | |

FOREIGN PATENT DOCUMENTS

| | | |
|---|---|---|
| EP | 0 699 898 A2 | 3/1996 |
| EP | 0 699 898 A3 | 3/1996 |
| EP | 1 335 199 A1 | 8/2003 |

* cited by examiner

*Primary Examiner*—Eric F. Winakur
(74) *Attorney, Agent, or Firm*—Lee & Morse, P.C.

(57) ABSTRACT

A method of measuring a concentration of a component in a subject includes setting an intensity relationship equation between a positive-order beam and a negative-order beam with respect to a reference matter at a particular wavelength, applying a light having a first wavelength band absorbed by the component and detecting an intensity of a positive-order beam output from the subject and an intensity of a negative-order beam output from the reference matter, the positive-order beam and the negative-order beam having a second wavelength band, calculating an intensity of a positive-order beam input to the subject by applying the intensity of the negative-order beam output from the reference matter to the intensity relationship equation, and calculating absorbance using the intensity of the positive-order beam output from the subject and the intensity of the positive-order beam input to the subject and measuring a concentration of the component using the absorbance.

19 Claims, 4 Drawing Sheets

METHOD AND APPARATUS FOR MEASURING A CONCENTRATION OF A COMPONENT IN A SUBJECT

BACKGROUND OF THE INVENTION

1. Field of the Invention

The present invention relates to a measurement of a concentration of a component in a subject. More particularly, the present invention relates to a method and apparatus for accurately measuring a concentration of a component in a subject, such as a bodily fluid in a human body, by removing a time difference between a measurement of a reference light and a measurement of a signal light.

2. Description of the Related Art

With overall improvements in quality of life and living conditions, interest in personal health has increased. As a result, a wide array of home medical equipment that allows people to easily monitor their personal health has been researched and developed. In a normal human body, bodily fluid is organically circulated and adjusted so that an amount of bodily fluid is maintained within a predetermined range. Bodily fluids include blood, urine, interstitial fluid, sweat, and saliva. In particular, concentrations of blood and urine (glucose and protein) are essential parameters in determining a person's state of health. In addition, concentrations of blood components, such as glucose, hemoglobin, bilirubin, cholesterol, albumin, creatinine, protein, and urea, play an important role in assessing a person's state of health.

When a human body is infected with a disease, a composition or a volume of a component in a bodily fluid changes, which may result in death. For example, a normal person's blood glucose concentration is about 80 mg/dl before a meal and about 120 mg/dl after a meal. In order to maintain such a normal glucose concentration, a human pancreas secretes an appropriate amount of insulin before or after the meal so that glucose can be absorbed into the liver and skeletal muscle cells. However, when the pancreas does not secrete an appropriate amount of insulin to maintain a normal blood glucose concentration due to a disease or other causes, an excessive amount of glucose exists in the blood, which causes diseases of the heart or liver, arteriosclerosis, hypertension, cataract, retinal bleeding, nerve damage, hearing loss, or visual impairment, all of which may cause serious problems including death. Accordingly, a technique of measuring a change in a bodily fluid in a human body is considered very important.

Methods of measuring the concentration of a component of bodily fluid include invasive methods of directly collecting a sample from a subject and gathering measurements on the collected part of the subject and noninvasive methods of gathering measurements without directly collecting a sample from a subject. Since invasive methods have many problems, techniques of easily analyzing components of bodily fluid using a noninvasive method have been continuously researched and developed. Conventionally, when measuring a component of bodily fluid, for example, blood glucose, blood is extracted, reacted with a reagent, and then analyzed by using a clinical analysis system or quantifying a change in the color of a test strip. When such a blood glucose test is performed daily, a patient suffers from pain resulting from the direct blood collection and is susceptible to infection. Moreover, since it is difficult to continuously monitor the blood glucose level, it is difficult to properly treat a patient in an emergency situation. In addition, use of disposable strips and reagents may be a financial burden on the patient. Furthermore, these disposable strips and reagents cause environmental contamination, and as such, require special treatment. Accordingly, development of a technique of measuring a blood glucose concentration without extracting blood is desired for monitoring and adjusting the blood glucose level of a diabetic or diagnosing a person's state of health. Many methods of noninvasively measuring blood glucose have been researched, but instruments using these methods have not been commercialized.

In most conventional, spectroscopic methods of measuring the concentration of a blood component in a human body, light within a visible ray and near infrared ray (NIR) wavelength range is radiated onto a part of the human body, and then, light reflected from or transmitted through the human body is detected. In such spectroscopic methods, a spectrum is usually measured to measure the concentration of a blood component. Here, a reference light source having a wavelength that responds best to a blood component to be measured and a bandwidth that effectively counterbalances an influence of an interference substance is required. Conventionally, a continuous wave (CW) lamp is used as a light source, and the intensity of the light is measured using an expensive array detector, or a spectrum is measured using a spectroscopic system, in order to calculate the concentration of a component. Alternatively, a light emitting diode (LED) or a laser diode (LD) may be used as the light source.

However, since the concentration of a component to be measured may be very low in blood and a light diffusion effect is greater than a light absorption effect in living tissue and blood, detected signals are very weak. Thus, a method of amplifying the signal is required. Moreover, since organic substances in a human body continuously flow, a component concentration can be accurately measured only when the measurement is quickly performed. In addition, it must be noted that an average energy radiated onto a human body should not go beyond a limit that may damage the human body. In particular, in an NIR wavelength range of 700 through 2500 nm, a glucose absorption band is widely distributed, but a maximum absorption of glucose is small as compared to a large aqueous background spectrum. Resultantly, a signal to noise ratio (SNR) is small, which makes accurate measurements very difficult.

In various conventional, non-invasive methods of measuring a concentration of a component in a subject, absorbance is measured, and a multivariate statistical analysis is performed on the absorbance to analyze a component concentration. The absorbance can be expressed as a negative log ratio between signal light intensity measured from a sample and reference light intensity. Since the reference light intensity measured without a human body and the signal light intensity measured from the human body are measured at predetermined time intervals, a time difference exists between the measurement of the signal light intensity and the measurement of the reference light intensity. Such a time difference can be removed by simultaneously measuring the reference light intensity and the signal light intensity. In a conventional approach for removing the time difference, a beam is split into two beams by a beam splitter before being radiated onto a human body. One of the two beams is sent to a reference light intensity channel, and the other is sent to a signal light intensity channel. Intensities of these two beams are separately measured and used to predict the concentration of a particular component. In this situation, however, an additional optical system for splitting an input beam and related parts are required. Therefore, it is difficult to construct a compact system. Meanwhile, when a beam splitter is not used, the reference light intensity is measured first, then the signal light intensity is measured in order to calculate absorbance. However, due to influences of various changes occurring during an interval of time between the measurement of the reference light intensity and the measurement of the signal light intensity, it is difficult to accurately predict the concentration of a component.

SUMMARY OF THE INVENTION

In an effort to solve at least some of the above problems, it is a feature of an embodiment of the present invention to provide a method of accurately measuring a concentration of a component in a subject by removing a time difference between a measurement of a reference light and a measurement of a signal light.

It is another feature of an embodiment of the present invention to provide an apparatus suitable for implementing the above-described method.

According to a feature of an embodiment of the present invention, there is provided an apparatus for measuring a concentration of a component in a subject including a light source that generates a light having a first wavelength band for the component, a radio frequency (RF) signal generator that generates a radio frequency (RF) signal having a predetermined frequency so that a light having a second wavelength band can be generated from the light having the first wavelength band, a tunable filter that receives the light having the first wavelength band and generates a positive-order beam and a negative-order beam, which have the second wavelength band, according to the RF signal provided by the RF signal generator, a first light detector that detects a first output beam reflected from or transmitted through the subject onto which the positive-order beam generated by the tunable filter has been radiated, a second light detector that detects a second output beam reflected from or transmitted through a reference matter onto which the negative-order beam generated by the tunable filter has been radiated, and a signal processor, which has been previously provided with an intensity relationship equation between the positive-order beam and the negative-order beam, that calculates an intensity of the positive-order beam input to the subject by applying an intensity of the second output beam from the reference matter to the intensity relationship equation, calculates absorbance using the intensity of the first output beam from the subject and the intensity of the positive-order beam input to the subject, and measures a concentration of the component using the absorbance.

The apparatus may further include a condenser lens on an optical path between the light source and the tunable filter to condense the light emitted from the light source. The light source may be a halogen lamp. The first and second light detectors may be photodetectors made of a material selected from the group consisting of InGaAs, PbS, and InSb. The tunable filter may include a transducer and an acoustic-optic medium and the acoustic-optic medium may be a crystal.

The apparatus may further include a beam guiding unit that guides the positive-order beam generated by the tunable filter to be transmitted to be parallel to the subject and guides the negative-order beam generated by the tunable filter to be transmitted to be parallel to the reference matter. The first and second beam guiding units may be selected from the group consisting of a tapered aluminum tube, a glass rod, and a hollow waveguide.

The apparatus may further include a refractive index matching unit, which is disposed between the beam guiding unit and the subject, to match an internal refractive index of the subject with an external refractive index of the subject.

In the apparatus, the signal processor may obtain the intensity relationship equation using a positive-order beam and a negative-order beam, which are output from the reference matter when a positive-order beam and a negative-order beam generated by the tunable filter at a particular wavelength are radiated onto the reference matter.

According to another feature of an embodiment of the present invention, there is provided a method of measuring a concentration of a component in a subject including setting an intensity relationship equation between a positive-order beam and a negative-order beam with respect to a reference matter at a particular wavelength, applying a light having a first wavelength band absorbed by the component and detecting an intensity of a positive-order beam output from the subject and an intensity of a negative-order beam output from the reference matter, the positive-order beam and the negative-order beam having a second wavelength band, calculating an intensity of a positive-order beam input to the subject by applying the intensity of the negative-order beam output from the reference matter to the intensity relationship equation, and calculating absorbance using the intensity of the positive-order beam output from the subject and the intensity of the positive-order beam input to the subject and measuring a concentration of the component using the absorbance.

In the method, setting the intensity relationship equation may include generating the positive-order and negative-order beams having the second wavelength band from the light, which has the first wavelength band and is provided from a light source, according to a radio frequency (RF) signal having a predetermined frequency, radiating the positive-order and negative-order beams onto the reference matter and detecting the intensities of the respective positive-order and negative-order beams output from the reference matter, and setting the intensity relationship equation based on the detected intensities of the positive-order and negative-order beams.

In the method, applying the light having the first wavelength band and detecting the intensities of the positive-order beam output from the subject and the negative-order beam output from the reference matter may include generating the positive-order and negative-order beams having the second wavelength band from the light, which has the first wavelength band and is provided from the light source, according to a radio frequency (RF) signal having a predetermined frequency and radiating the generated positive-order and negative-order beams onto the subject and the reference matter, respectively, and detecting the intensity of the positive-order beam output from the subject and the intensity of the negative-order beam output from the reference matter.

According to yet another feature of an embodiment of the present invention, there is provided a computer readable recording medium having recorded therein a program for executing the above method.

BRIEF DESCRIPTION OF THE DRAWINGS

The above and other features and advantages of the present invention will become more apparent to those of ordinary skill in the art by describing in detail preferred embodiments thereof with reference to the attached drawings in which.

DETAILED DESCRIPTION OF THE INVENTION

Korean Patent Application No. 2003-16406, filed on Mar. 17, 2003, and entitled: "Method and Apparatus for Measuring Concentration of Component in a Subject," is incorporated by reference herein in its entirety.

The present invention will now be described more fully hereinafter with reference to the accompanying drawings, in which preferred embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

Figure 1:
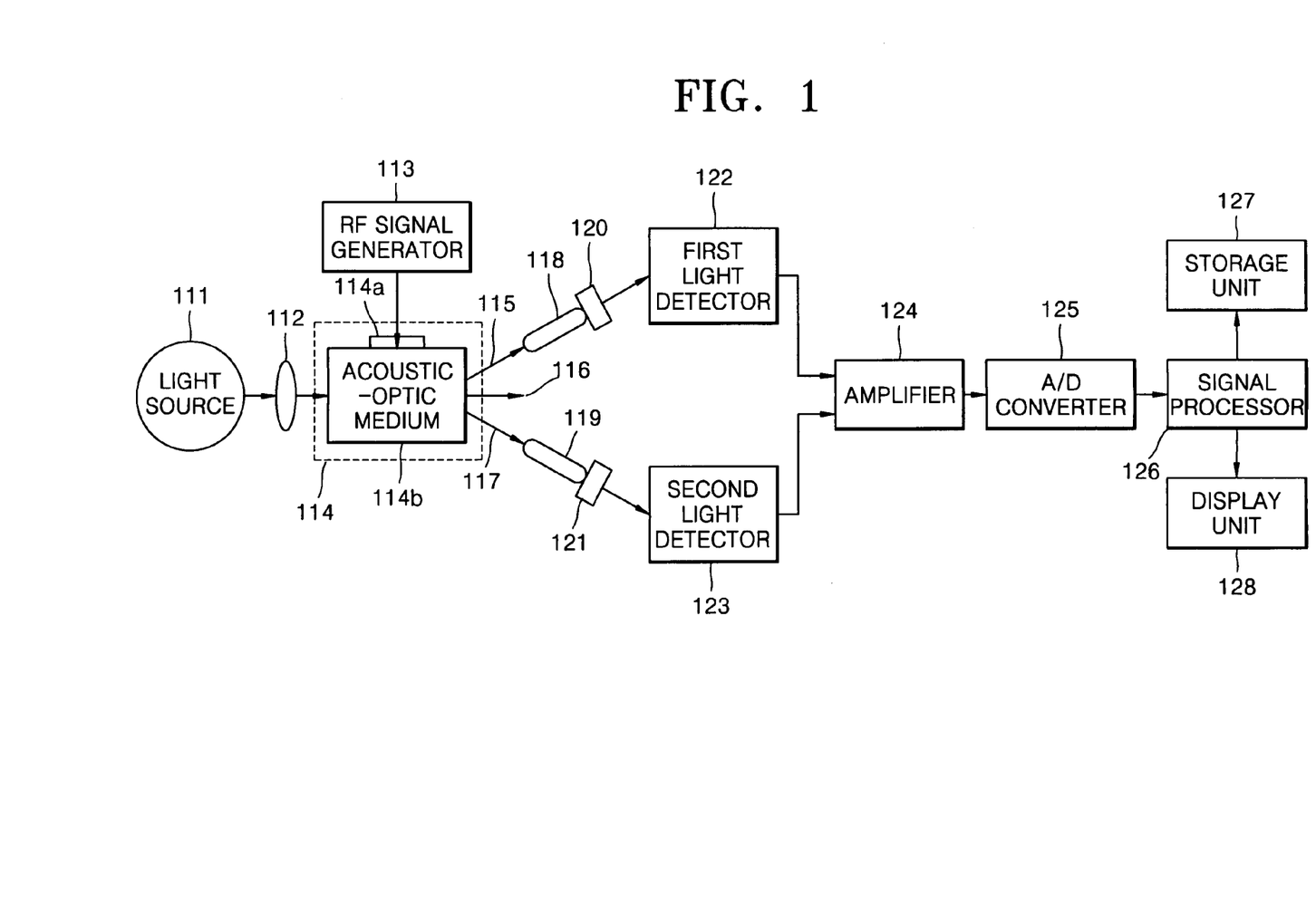
FIG. 1 is a block diagram of an apparatus for measuring a concentration of a component in a subject according to an embodiment of the present invention.

FIG. 1 is a block diagram of an apparatus for measuring a concentration of a component in a subject according to an embodiment of the present invention. The apparatus includes a light source 111, a condenser lens 112, a radio frequency (RF) signal generator 113, a tunable filter 114, a first beam guiding unit 118, a second beam guiding unit 119, a first light detector 122, a second light detector 123, an amplifier 124, an analog-to-digital (A/D) converter 125, a signal processor 126, a storage unit 127, and a display unit 128. The light source 111, the condenser lens 112, the RF signal generator 113, the tunable filter 114, and the first and second beam guiding units 118 and 119 constitute a light radiation unit. Reference numerals 115, 116, and 117 denote positive-order, zero-order, and negative-order beams, respectively, which are generated by the tunable filter 114. Reference numeral 120 denotes a subject to be measured, and reference numeral 121 denotes a reference matter contained in a container. The reference matter 121 is a subject having 100% permeability. Accordingly, an intensity of a beam input to the reference matter 121 is the same as that of a beam output from the reference matter 121. The reference matter 121 may be replaced with a container, e.g., a cuvette, which is empty.

In operation, the light source 111 emits a light signal having a particular wavelength band absorbed by a particular component in a human bodily fluid. The particular component to be measured, which may be glucose, hemoglobin, albumin, or cholesterol, absorbs light having a particular wavelength according to its respective characteristics. Various types of lamps may be used as the light source 111 according to the particular component to be measured. In this embodiment of the present invention, a halogen lamp is used as the light source 111.

The condenser lens 112 is fixed on an optical path of the light source 111 to condense the light signal emitted from the light source 111. The light signal condensed by the condenser lens 112 is applied to the tunable filter 114. The condenser lens 112 is optional and may be omitted or incorporated, if required by a particular application.

The RF signal generator 113 generates an RF signal to vary a wavelength of the light signal applied to the tunable filter 114 through the condenser lens 112, if present, and provides the RF signal to the tunable filter 114. It is preferable that the RF signal has a frequency enabling the tunable filter 114 to generate light having a wavelength ranging from 400 to 12,000 nm. The tunable filter 114 is preferably implemented by an acoustic-optic device having a wide tuning range and a fast tuning speed so as to perform wavelength scanning in microseconds (μs). The tunable filter 114 includes a transducer 114a and an acoustic-optic medium 114b, for example, crystal.

An operation of the RF signal generator 113 will be described in association with an operation of the tunable filter 114. Upon receiving an external electrical signal, the RF signal generator 113 provides the RF signal to the transducer 114a in combination with the acoustic-optic medium 114b. The transducer 114a generates and provides an ultrasonic wavefront to the acoustic-optic medium 114b. A light beam incident from the light source 111 interacts with the ultrasonic wavefront within the acoustic-optic medium 114b to generate positive-order beams and negative-order beams by satisfying the Bragg condition. A portion of the incident light beam is output as it is and becomes a zero-order beam. More specifically, a wavelength of light applied to the tunable filter 114 varies with a frequency of the RF signal provided from the RF signal generator 113, and the light is output as the positive-order beam 115, the zero-order beam 116, and the negative-order beam 117 having a same reflection order as the positive-order beam 115, according to a diffraction angle of the acoustic-optic medium 114b. The positive-order beam 115 is provided to the first beam guiding unit 118, and the negative-order beam 117 is provided to the second beam guiding unit 119. Here, the positive-order beam 115 may have a reflection order of +1, and the negative-order beam 117 may have a reflection order of −1. The zero-order beam 116 is not used and is thus blocked. Either the positive-order beam 115 or the negative-order beam 117 may be used as a signal light. In this embodiment, the positive-order beam 115 is used as the signal light, and the negative-order beam 117 is used as an auxiliary light to calculate a reference light.

The first beam guiding unit 118 transmits the positive-order beam 115 to be parallel, and the second beam guiding unit 119 transmits the negative-order beam 117 to be parallel. The first and second beam guiding units 118 and 119 may each be implemented by a tapered aluminum tube, a glass rod, or a hollow waveguide. The positive-order beam 115 and the negative-order beam 117 are radiated onto the subject 120 and the reference matter 121 contained in the container, respectively. The subject 120 may be a part of a human body, such as a finger or an ear lobe, in vivo or may be a predetermined container, such as cuvette, capable of containing a sample in vitro. Accordingly, when the subject 120 is a vital tissue, the concentration of a component is measured non-invasively. When the subject 120 is a sample cuvette, the concentration of a component is measured invasively.

Since a refractive index of the surface of the vital tissue including blood is different from that of the inside of the vital tissue, a refractive index matching unit can be additionally disposed between the first beam guiding unit 118 and the subject 120 to match an internal refractive index of the subject 120 with an external refractive index of the subject 120 so that a signal to noise ratio (SNR) can be significantly increased.

The first light detector 122 detects a signal light transmitted through or reflected from the subject 120 and provides it to the amplifier 124. The second light detector 123 detects reference light generated from the reference matter 121 contained in the container and provides it to the amplifier 124. The first and second light detectors 122 and 123 may be implemented by a photodetector made of InGaAs, PbS, or InSb. The amplifier 124 amplifies the signal light and the reference light detected by the first and second light detectors 122 and 123, respectively, to a predetermined level. The amplified signal light and the amplified reference light are converted into digital data by the A/D converter 125 and then provided to the signal processor 126.

The signal processor 126 is usually implemented by a microprocessor and is provided with an intensity relationship equation between a positive-order beam and a negative-order beam and an algorithm for predicting the concentration of a component. The signal processor 126 processes and analyzes the digital data received from the A/D converter 125, calculates absorbance using the intensity of the reference light and the intensity of the signal light, and calculates the concentration of a particular component using the prediction algorithm. More specifically, a model prediction formula for accurately predicting concentrations of different components can be made by comparing and analyzing absorbances with respect to different wavelengths, and the concentration of a particular component can be calculated using the model prediction formula and the calculated absorbance.

The storage unit 127 stores the result of the processing performed by the signal processor 126. The display unit 128 displays the result of the processing on a screen.

Figure 2:
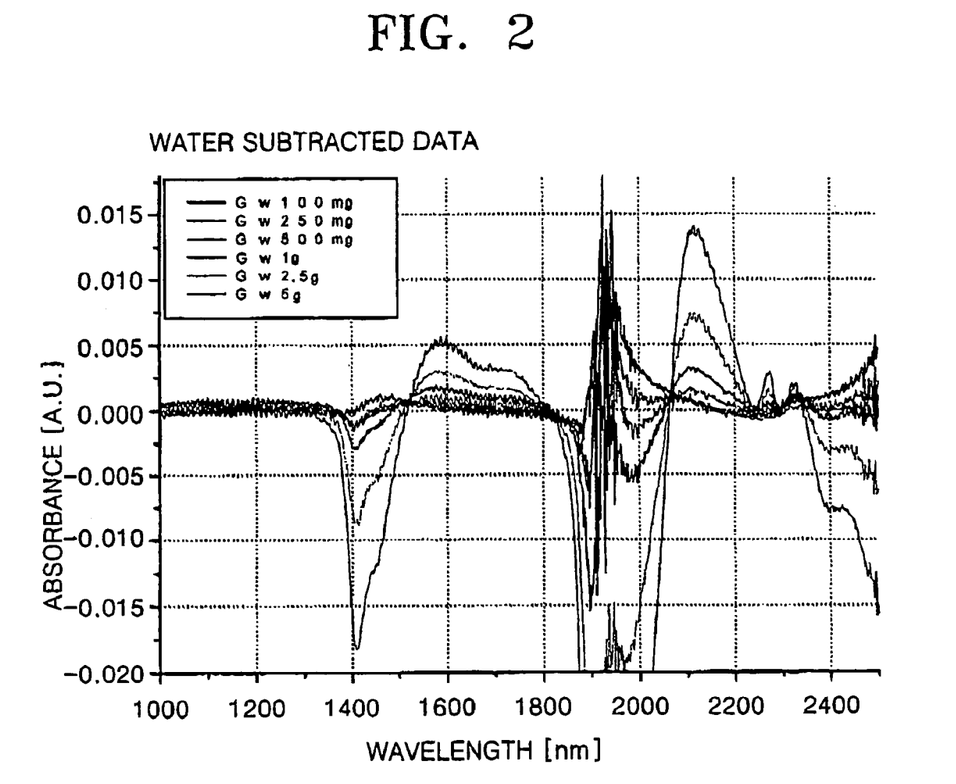
FIG. 2 is a graph showing absorption spectrums at different wavelengths when water is subtracted from an aqueous glucose solution.

FIG. 2 is a graph showing absorption spectrums measured at a path length of 0.5 mm using a spectroscopic system when a concentration of glucose in an aqueous glucose solution changes. These absorption spectrums correspond to absorption spectrums obtained when water is subtracted from the aqueous glucose solution. As shown in FIG. 2, absorbance of glucose is large at a wavelength ranging from 1500 to 1700 nm and a wavelength of 2100 nm. Accordingly, in order to measure the concentration of glucose, a frequency of the RF signal from the RF signal generator 113 is adjusted so that the light provided by the tunable filter 114 includes a wavelength range from 1500 to 1700 nm and a wavelength of 2100 nm.

Figure 3:
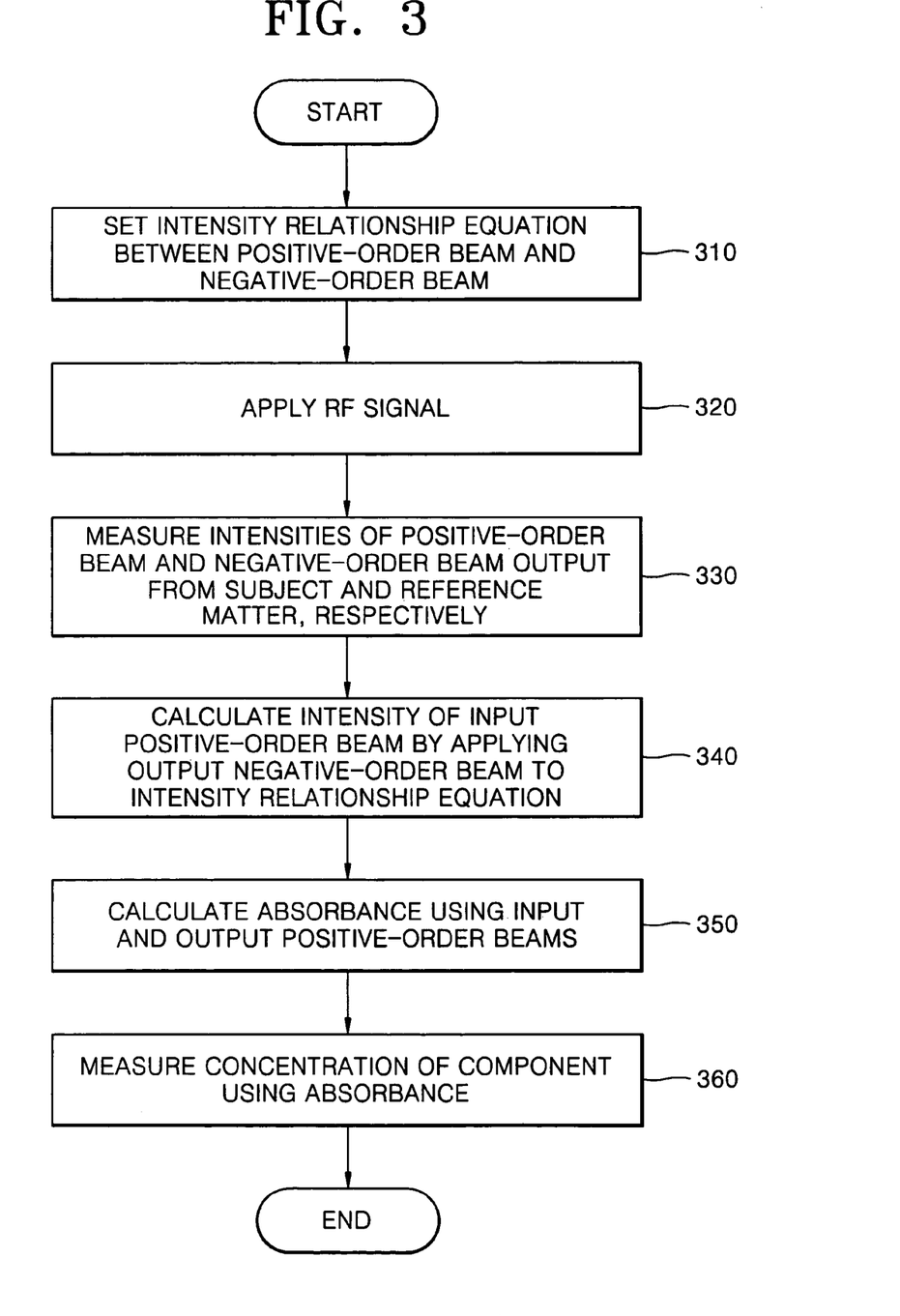
FIG. 3 is a flowchart of a method of measuring a concentration of a component in a subject according to an embodiment of the present invention.

FIG. 3 is a flowchart of a method of measuring a concentration of a component in a subject according to an embodiment of the present invention. Referring to FIG. 3, in operation 310, an intensity relationship equation between a positive-order beam and a negative-order beam is set. Operation 310 will be described in greater detail with reference to FIG. 4.

Figure 4:
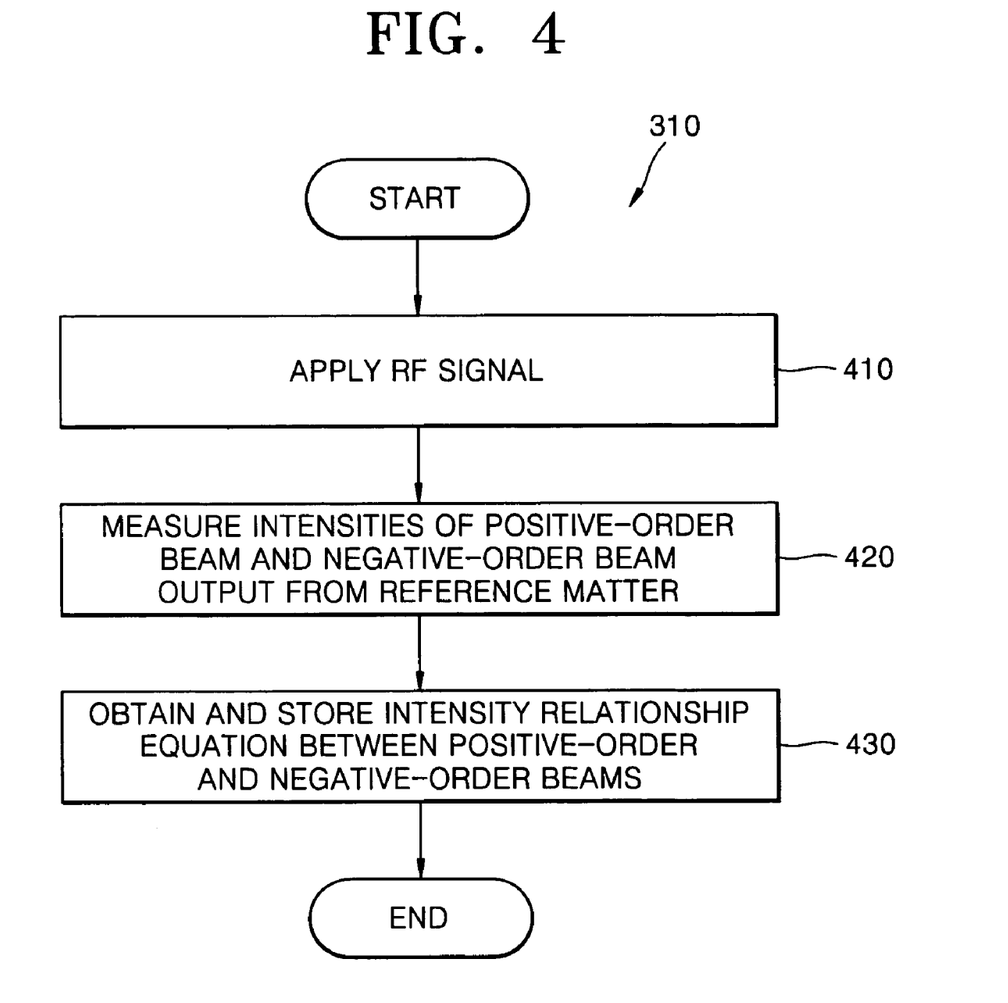
FIG. 4 is a detailed flowchart of operation 310 shown in FIG. 3.

In operation 410 of FIG. 4, the RF signal generator 113 applies an RF signal for generating a particular wavelength to the tunable filter 114. For example, when a concentration of glucose is to be measured, an RF signal having a frequency of 54–119 MHz is applied so that the tunable filter 114 can output light having a wavelength range of 1200–2400 nm, which includes a wavelength ranging from 1500 to 1700 nm and a wavelength of 2100 nm.

In operation 420, a second reference matter (not shown) is substituted for the subject 120 so that the positive-order beam 115 and the negative-order beam 117 generated by the tunable filter 114 according to the RF signal are both radiated onto the reference matter 121 in the container, and an intensity of a positive-order beam output from the reference matter and an intensity of a negative-order beam output from the reference matter may be measured. In operation 430, an intensity relationship equation (y=kx, where k is a constant) between a positive-order beam and a negative-order beam is obtained from the intensity (y) of the positive-order beam and the intensity (x) of the negative-order beam output from the reference matter 121. The intensity relationship equation is then stored together with a wavelength of light applied to the tunable filter 114, the wavelength of the light generated by the tunable filter 114, and/or the frequency of the RF signal in the signal processor 126 in the form of a database.

Referring back to FIG. 3, in operation 320, the RF signal generator 113 applies an RF signal having a predetermined frequency to the tunable filter 114 to generate light having a second wavelength band from light having a first wavelength band emitted from the light source 111.

In operation 330, the positive-order beam 115 and the negative-order beam 117 are generated by the tunable filter 114 according to the RF signal and radiated onto the subject 120 and the reference matter 121, respectively, through the first and second beam guiding units 118 and 119, so that a positive-order beam and a negative-order beam respectively output from the subject 120 and the reference matter 121 are acquired. Intensities of the positive-order beam output from the subject 120 and the negative-order beam output from the reference matter 121 are then measured.

In operation 340, an intensity (y) of the positive-order beam output from the reference matter 121 is calculated by applying the intensity (x) of the negative-order beam output from the reference matter 121 obtained in operation 330 to the intensity relationship equation (y=kx) set in operation 310. Since the reference matter 121 has 100% permeability, the intensity of the beam input to the reference matter 121 is the same as that of the beam output from the reference matter 121. Thus, the calculated intensity (y) of the positive-order beam output from the reference matter 121 becomes the intensity of the positive-order beam input to the reference matter 121, i.e., the intensity of the positive-order beam input to the subject 120.

In operation 350, absorbance is calculated using the positive-order beam output from the subject 120 obtained in operation 330 and the positive-order beam output from the reference matter 121 obtained in operation 340, i.e., the positive-order beam input to the subject 120.

In operation 360, a concentration of the component is measured using the absorbance. More specifically, the intensity of the positive-order beam output from the subject 120 is set as a signal light intensity, the intensity of the positive-order beam input to the subject 120 is set as a reference light intensity, and a negative log ratio between the signal light intensity and the reference light intensity is calculated to determine the absorbance.

When the subject 120 is a human body, the intensity of a positive-order beam output from the subject 120 is directly detected by the first light detector 122. The intensity of a positive-order beam input to the subject 120 is calculated by applying a negative-order beam output from the reference matter 121 and detected by the second light detector 123 to the previously provided intensity relationship equation between a positive-order beam and a negative-order beam. Accordingly, the intensity of an input beam of the subject 120 and the intensity of an output beam of the subject 120 can be simultaneously measured without a measurement time difference. Thus, the actual concentration of a component can be accurately calculated using absorbance calculated from the intensities of the input and output beams and an algorithm for predicting a concentration of the component. The algorithm can be obtained using a multivariate regression method, such as a partial least squares regression (PLSR) method.

The present invention can be realized as a code which is recorded on a computer readable recording medium and can be read by a computer. The computer readable recording medium may be any type of medium on which data that can be read by a computer system can be recorded, for example, a ROM, a RAM, a CD-ROM, a magnetic tape, a floppy disc, or an optical data storage device. The present invention can also be realized as carrier waves (for example, transmitted through Internet). Alternatively, computer readable recording media may be distributed among computer systems connected through a network so that the present invention may be realized as a code that is stored in the recording media and can be read and executed in computers. Functional programs, codes, and code segments for implementing the present invention can be easily inferred by programmers in the art of the present invention.

As described above, in the present invention, a difference between a measurement time of a reference light intensity and a signal light intensity is removed. In the present invention, the reference light intensity is obtained without encountering a subject to be measured, i.e., an intensity of an input beam of the subject, and a measurement time of a signal light intensity is obtained when the subject is encountered, i.e., an intensity of an output beam of the subject. Because the measurement time difference is removed, an accurate concentration of a component of a subject, such as bodily fluid, can be invasively or non-invasively measured without being influenced by various changes occurring during a conventional measurement time difference.

In addition, since a tunable filter composed of an acoustic-optic device is used without using any moving mechanical elements, influence of an external environment, such as a vibration or a shock, is reduced, and fast wavelength scanning is possible. Moreover, a spectrum bandwidth of a light source can be freely controlled by adjusting the frequency of an RF signal applied to the tunable filter. Therefore, the concentration of a component having a narrow absorption band can be easily measured.

Preferred embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A method of measuring a concentration of a component in a subject, comprising:
   setting an intensity relationship equation between a positive-order beam and a negative-order beam with respect to a reference matter at a particular wavelength by measuring both the positive-order and negative-order beams output from the reference matter;
   applying a light having a first wavelength band absorbed by the component and detecting an intensity of a positive-order beam output from the subject and an intensity of a negative-order beam output from the reference matter, the positive-order beam and the negative-order beam having a second wavelength band;
   calculating an intensity of a positive-order beam input to the subject by applying the intensity of the negative-order beam output from the reference matter to the intensity relationship equation; and
   calculating absorbance using the intensity of the positive-order beam output from the subject and the intensity of the positive-order beam input to the subject and measuring a concentration of the component using the absorbance.

2. The method as claimed in claim 1, wherein setting the intensity relationship equation comprises:
   generating the positive-order and negative-order beams having the second wavelength band from the light, which has the first wavelength band and is provided from a light source, according to a radio frequency (RF) signal having a predetermined frequency;
   radiating the positive-order and negative-order beams onto the reference matter and detecting the intensities of the respective positive-order and negative-order beams output from the reference matter; and
   setting the intensity relationship equation based on the detected intensities of the positive- order and negative-order beams.

3. The method as claimed in claim 2, wherein setting the intensity relationship includes storing intensity relationship equations corresponding to at least one of the first wavelength band, the second wavelength band and the RE signal.

4. The method as claimed in claim 1, wherein applying the light having the first wavelength band and detecting the intensities of the positive-order beam output from the subject and the negative-order beam output from the reference matter comprises:
   generating the positive-order and negative-order beams having the second wavelength band from the light, which has the first wavelength band and is provided from the light source, according to a radio frequency (RF) signal having a predetermined frequency; and
   radiating the generated positive-order and negative-order beams onto the subject and the reference matter, respectively; and
   detecting the intensity of the positive-order beam output from the subject and the intensity of the negative-order beam output from the reference matter.

5. A computer readable recording medium having recorded therein a program for executing the method as claimed in claim 1.

6. The method as claimed in claim 1, wherein setting the intensity relationship includes storing intensity relationship equations corresponding to at least one of the first wavelength band and the second wavelength band.

7. An apparatus for measuring a concentration of a component in a subject, comprising:
   a light source that generates a light having a first wavelength band for the component;
   a tunable filter that receives the light having the first wavelength band and generates a positive-order beam and a negative-order beam, which have a second wavelength band, according to a tuning signal applied thereto;
   a first light detector that detects a first output beam reflected from or transmitted through the subject onto which the positive-order beam generated by the tunable filter has been radiated;
   a second light detector that detects a second output beam reflected from or transmitted through a reference matter onto which the negative-order beam generated by the tunable filter has been radiated; and
   a signal processor, which has been previously provided with an intensity relationship equation between the positive-order beam and the negative-order beam obtained by measuring both the positive-order and negative-order beams output from the reference matter, that calculates an intensity of the positive-order beam input to the subject by applying an intensity of the second output beam from the reference matter to the intensity relationship equation, calculates absorbance using the intensity of the first output beam from the subject and the intensity of the positive-order beam input to the subject, and measures a concentration of the component using the absorbance.

8. The apparatus as claimed in claim 7, further comprising a condenser lens on an optical path between the light source and the tunable filter to condense the light emitted from the light source.

9. The apparatus as claimed in claim 7, wherein the light source is a halogen lamp.

10. The apparatus as claimed in claim 7, wherein the first and second light detectors are photodetectors made of a material selected from the group consisting of InGaAs, PbS, and InSb.

11. The apparatus as claimed in claim 7, wherein the tunable filter comprises:
a transducer; and
an acoustic-optic medium.

12. The apparatus as claimed in claim 11, wherein the acoustic-optic medium is a crystal.

13. The apparatus as claimed in claim 7, further comprising a beam guiding unit that guides the positive-order beam generated by the tunable filter to be transmitted to be parallel to the subject and guides the negative-order beam generated by the tunable filter to be transmitted to be parallel to the reference matter.

14. The apparatus as claimed in claim 13, further comprising a refractive index matching unit, which is disposed between the beam guiding unit and the subject, to match an internal refractive index of the subject with an external refractive index of the subject.

15. The apparatus as claimed in claim 7, wherein the first and second beam guiding units are selected from the group consisting of a tapered aluminum tube, a glass rod, and a hollow waveguide.

16. The apparatus as claimed in claim 7, wherein the signal processor obtains the intensity relationship equation using a positive-order beam and a negative-order beam, which are output from the reference matter when a positive-order beam and a negative-order beam generated by the tunable filter at a particular wavelength are radiated onto the reference matter.

17. The apparatus as claimed in claim 7, further comprising a radio frequency (RF) signal generator that generates a radio frequency (RF) signal having a predetermined frequency, the RF signal serving as the tuning signal for the tunable filter.

18. The apparatus as claimed in claim 17, wherein the signal processor stores intensity relationship equations corresponding to at least one of the first wavelength band and the second wavelength band and the RF signal.

19. The apparatus as claimed in claim 7, wherein setting the intensity relationship includes storing intensity relationship equations corresponding to at least one of the first wavelength band, the second wavelength band and the tuning signal.

* * * * *